United States Patent
Kenry et al.

(10) Patent No.: US 10,488,276 B2
(45) Date of Patent: Nov. 26, 2019

(54) RESISTIVE MICROFLUIDIC PRESSURE SENSOR

(71) Applicant: NATIONAL UNIVERSITY OF SINGAPORE, Singapore (SG)

(72) Inventors: Kenry, Singapore (SG); Joo Chuan Yeo, Singapore (SG); Chwee Teck Lim, Singapore (SG)

(*) Notice: Subject to any disclaimer, the term of this patent is extended or adjusted under 35 U.S.C. 154(b) by 0 days.

(21) Appl. No.: 15/559,617

(22) PCT Filed: Mar. 23, 2016

(86) PCT No.: PCT/SG2016/050133
§ 371 (c)(1),
(2) Date: Sep. 19, 2017

(87) PCT Pub. No.: WO2016/153429
PCT Pub. Date: Sep. 29, 2016

(65) Prior Publication Data
US 2018/0067000 A1    Mar. 8, 2018

Related U.S. Application Data

(60) Provisional application No. 62/137,391, filed on Mar. 24, 2015.

(51) Int. Cl.
G01L 1/20 (2006.01)
G01L 1/02 (2006.01)
G01L 1/22 (2006.01)
G01L 5/22 (2006.01)
(Continued)

(52) U.S. Cl.
CPC ............. *G01L 1/02* (2013.01); *G01L 1/20* (2013.01); *G01L 1/22* (2013.01); *G01L 5/226* (2013.01); *A61B 5/225* (2013.01); *G06F 3/014* (2013.01)

(58) Field of Classification Search
CPC ...... H01C 17/28; G01B 7/16; A61M 5/16877; A61M 5/36; A61M 2205/0244; A61M 5/141; A61M 2205/3331; G01R 33/302; Y10T 137/8326; Y10T 137/0318; Y10T 137/8593; G01N 27/414; H01L 29/1606; H01L 29/66; H01L 29/66053; B01L 3/502707
See application file for complete search history.

(56) References Cited

U.S. PATENT DOCUMENTS 7,854,173 B2 * 12/2010 Cheng .................. G01B 7/18
                                                      73/760
8,950,266 B2    2/2015 Dickey et al.
(Continued)

FOREIGN PATENT DOCUMENTS

JP    2011-232322 A    11/2011
JP    2013-35966 A     2/2013
WO   WO 2013/044226 A2    3/2013

*Primary Examiner* — Brandi N Hopkins
(74) *Attorney, Agent, or Firm* — QIPLG; Gary Baker

(57) ABSTRACT

A resistive microfluidic pressure sensor is provided which comprises a first layer comprising a microfluidic channel with a carbon-based conductive liquid and a second layer comprising at least two electrodes, the at least two electrodes being adapted to measure resistance of the carbon-based conductive liquid upon deformation of the microfluidic channel as a result of a change in force applied on a surface of the sensor.

15 Claims, 13 Drawing Sheets

(51) Int. Cl.
*A61B 5/22* (2006.01)
*G06F 3/01* (2006.01)

(56) References Cited

U.S. PATENT DOCUMENTS

| | | | | |
|---|---|---|---|---|
| 2007/0028683 | A1* | 2/2007 | Ionescu-Zanetti | A61B 5/021 73/299 |
| 2009/0007685 | A1 | 1/2009 | Cheng et al. | |
| 2013/0312541 | A1* | 11/2013 | Majidi | G01B 7/18 73/862.454 |
| 2013/0334579 | A1* | 12/2013 | Accardi | G01N 27/414 257/253 |
| 2014/0320948 | A1* | 10/2014 | Suzuki | G02B 26/005 359/290 |

* cited by examiner

Original state

Rough surface

Smooth surface

RESISTIVE MICROFLUIDIC PRESSURE SENSOR

TECHNICAL FIELD

The present invention relates to a resistive microfluidic pressure sensor, particularly to a flexible resistive microfluidic pressure sensor.

BACKGROUND

Microfluidics-based sensing devices, specifically, have been used for various chemical and biological assays, cellular manipulations, and electronic skin applications due to its exceptional sensitivity, flexibility, and adaptability. By utilizing only a minute quantity of conductive liquid (e.g., metallic or ionic liquid), responses to an external load may be detected in a microfluidic-based device through alterations in the geometry or physical properties of the working liquid, such as variations in its capacitance. With the intrinsic mechanical deformability of liquids, the liquid-state device technology offers a suitable avenue for the advancement of conformal devices capable of undergoing an extreme degree of deformation without the conventional solid-state materials-associated plastic deformation, fracture, and delamination. In considering the liquid materials to be used in the microfluidics-based sensors, working fluid with low viscosity and high physicochemical stability is highly advantageous.

Commonly used microfluidics-based sensing devices are based on detection by measuring capacitance. It is generally more complicated to measure the force of the external loads.

Further, with its far-reaching technological impacts, pressure sensing is one of the most critical components for a wide range of emerging applications such as in soft robotics, wearable consumer electronics, smart medical prosthetic devices and electronics skins, and real-time healthcare monitoring. As the demands for these applications continue to soar, the demands for pressure sensing are likewise becoming more stringent, particularly that of lightweight, flexible, and low cost.

There is therefore a need for an improved pressure sensor which is able to achieve reliable measurements in a simple and cost effective manner, while being suitable for use in at least the applications stated above.

SUMMARY OF THE INVENTION

The present invention seeks to address these problems, and/or to provide an improved microfluidic pressure sensor.

In general terms, the invention relates to a resistive microfluidic pressure sensor. In particular, the resistive microfluidic pressure sensor is simple and relatively cheap to manufacture while having superior mechanical deformability and integrity, thereby being suitable in wide-spread applications.

According to a first aspect, the present invention provides a resistive microfluidic pressure sensor comprising:
  a first layer comprising a microfluidic channel, the microfluidic channel comprising a carbon-based conductive liquid; and
  a second layer comprising at least two electrodes, the at least two electrodes being adapted to measure resistance of the carbon-based conductive liquid upon deformation of the microfluidic channel as a result of a change in force applied on a surface of the sensor.

In particular, application of the force on the surface of the sensor causes deformation of the microfluidic channel, thereby decreasing the cross-sectional area of the microfluidic channel and increasing the resistance of the carbon-based conductive liquid. The force applied on the surface of the sensor may be any suitable force. For example, the force may be a pressing force, bending force, shearing force and/or stretching force.

According to a particular aspect, the resistive microfluidic pressure sensor may be flexible.

The carbon-based conductive liquid may comprise graphene, graphene oxide, reduced graphene oxide, graphite, fullerene, carbon nanotubes, carbon black, functionalised carbon-based nanomaterials, or a combination thereof. In particular, the carbon-based conductive liquid may be graphene oxide. The graphene oxide may have any suitable concentration. For example, the concentration of the graphene oxide may be $\geq 0.2$ mg/mL. In particular, the concentration of the graphene oxide may be $\geq 0.5$ mg/mL, $\geq 1.0$ mg/mL, $\geq 1.5$ mg/mL, $\geq 2.0$ mg/mL, $\geq 2.5$ mg/mL, $\geq 3.0$ mg/mL, $\geq 3.5$ mg/mL. Even more in particular, the concentration of the graphene oxide may be $\geq 3.0$ mg/mL.

According to a particular aspect, the first layer and the second layer may be of the same or different material. In particular, the first layer and the second layer may be formed from an elastomeric material. The first layer and the second layer may be made from any suitable elastomeric material. In particular, the first layer and the second layer may comprise silicone rubber, polydimethylsiloxane (PDMS), polybutyrate, polyethylene terephthalate (PET), polycarbonate (PC), polyimide (PI), or a combination thereof. Even more in particular, the first layer and the second layer may be silicone rubber and PDMS, respectively.

According to another particular aspect, the first layer and the second layer are arranged to seal the carbon-based conductive liquid within the microfluidic channel, the carbon-based conductive liquid being interposed between the first layer and the second layer.

According to a second aspect, there is provided a wearable device for pressure sensing. In particular, the wearable device comprises the resistive microfluidic pressure sensor as described above.

BRIEF DESCRIPTION OF THE DRAWINGS

In order that the invention may be fully understood and readily put into practical effect there shall now be described by way of non-limitative example only exemplary embodiments, the description being with reference to the accompanying illustrative drawings. In the drawings:

FIG. 10 shows the plots showing the relative changes in the electrical resistances of the pressure sensor against dynamic movements of the fingers.

DETAILED DESCRIPTION

Figure 1A:
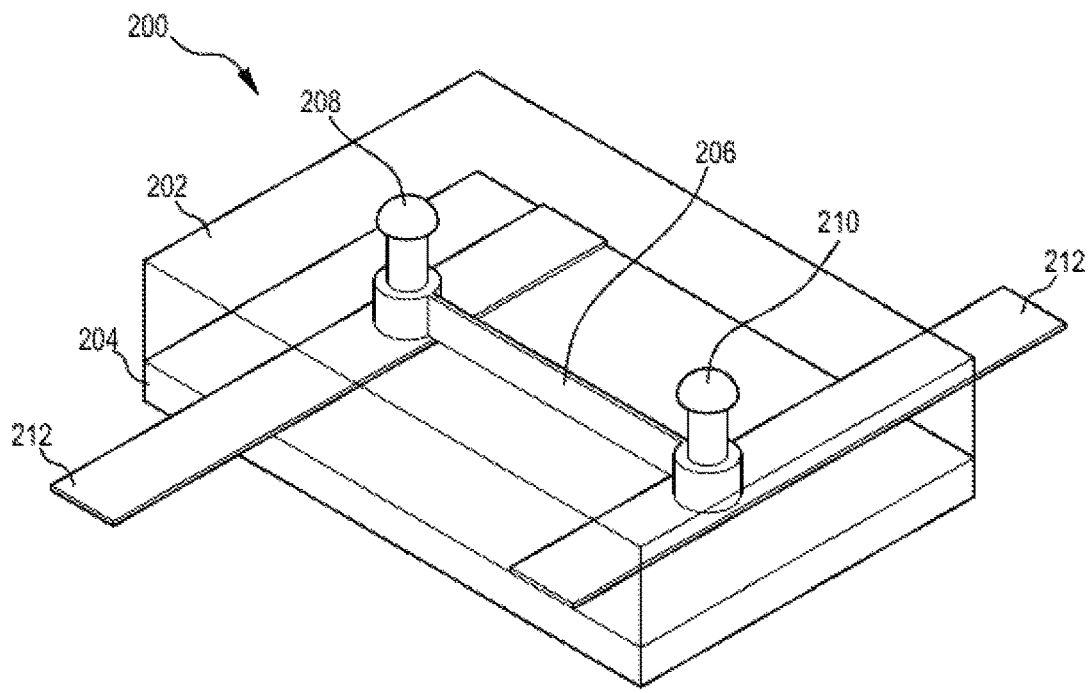
FIG. 1A shows a schematic representation of a resistive microfluidic pressure sensor according to one embodiment of the present invention and FIG. 1B shows a photograph of a resistive microfluidic pressure sensor according to one embodiment of the present invention.

The present invention provides a resistive microfluidic pressure sensor. The resistive microfluidic pressure sensor may be a flexible and conformal resistive pressure sensor which comprises a conductive liquid enclosed within a microfluidic channel within the microfluidic pressure sensor. In particular, the specific increase and decrease in the electrical resistances of the conductive liquid corresponds to the characteristic responses of different mechanical forces applied on the pressure sensor.

The resistive microfluidic pressure sensor may be highly flexible and capable of withstanding and distinguishing the various mechanical deformations applied onto it, like pressing, stretching, shearing, and bending. Furthermore, the pressure sensor is highly conformable, wearable, and able to differentiate numerous hand muscle-stimulated motions, such as finger flexing and fist clenching. Subtle differences in the handgrip strength resulted from the fist clenching motion may be identified with the use of the pressure sensor. These attributes render the resistive microfluidic pressure sensor as described herein an attractive and ideal platform for real-time and in situ health monitoring as well as for disease diagnosis and prognosis.

The resistive microfluidic pressure sensor may also be capable of detecting various surface textures. For example, subtle changes in the surface texture may elicit different electrical signatures with the use of the sensor.

The resistive microfluidic pressure sensor described is also easy to manufacture and its manufacturing process can therefore be easily scaled up without requiring complex and expensive equipment.

According to a first aspect, there is provided a resistive microfluidic pressure sensor comprising:
- a first layer comprising a microfluidic channel, the microfluidic channel comprising a carbon-based conductive liquid; and
- a second layer comprising at least two electrodes, the at least two electrodes being adapted to measure resistance of the carbon-based conductive liquid upon deformation of the microfluidic channel as a result of a change in force applied on a surface of the sensor.

In particular, the resistive microfluidic pressure sensor is flexible.

The resistive microfluidic pressure sensor may comprise a tactile sensor. For the purposes of the present invention, the resistive microfluidic pressure sensor 200 may be defined as a device which is capable of detecting a mechanical deformation exerted by a mechanical force and/or movement, and measuring the force or movement as an electrical signal or an alternative measurable output.

The pressure sensor according to the present invention is a resistive pressure sensor. Accordingly, the resistive pressure sensor is capable of detecting and measuring pressure as a change in the sensor electrical resistance or voltage due to deformation of the cross-sectional area of the sensor under applied pressure. This is in contrast to capacitive pressure sensors which measure pressure based on a change in dielectric properties due to material properties or displacement between two vertical plates. Resistive pressure sensors are easier to manufacture and assemble and require simple instrumentation for measurements.

FIG. 1A shows a resistive microfluidic pressure sensor 200 comprising a first layer 202 and a second layer 204. The first layer 202 comprises a microfluidic channel 206 which contains a carbon-based conductive liquid. The first layer 202 also comprises an inlet 208 and an outlet 210. The inlet 208 and the outlet 210 may be of any suitable size. For example, the inlet 208 and the outlet 210 may each be about 1-3 mm in diameter. In particular, the inlet 208 and the outlet 210 may each be about 1.2 mm in diameter.

The second layer 204 comprises two electrodes 212. The electrodes 212 may be placed at opposite ends of the microfluidic channel 206. The first layer 202 and the second layer 204 may be bonded together to form a sealed chamber of conductive liquid (not shown) interposed between the two electrodes 212.

The electrodes 212 may be any suitable electrodes. For example, the electrodes 212 may be, but not limited to metallic tapes, wires, conductive grease, conductive ink or a conductive film. In particular, the metallic tapes may be copper tapes, the conductive ink may be screen printed conductive ink, or the conductive film may be ITO film. Even more in particular, the electrodes 212 may be copper tapes. The electrodes 212 may be placed at opposite ends of the microfluidic channel 206 to obtain an electrical signal.

The inlet 208 and the outlet 210 may be sealed to confine the conductive liquid within the resistive microfluidic pressure sensor 200.

Figure 1B:
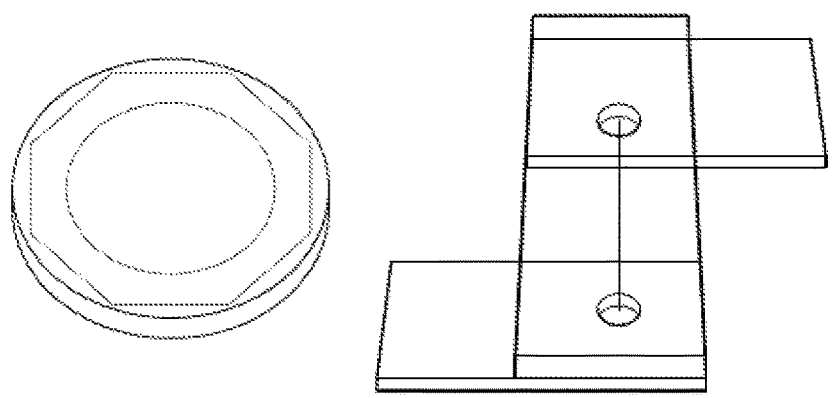
Figure 1B:
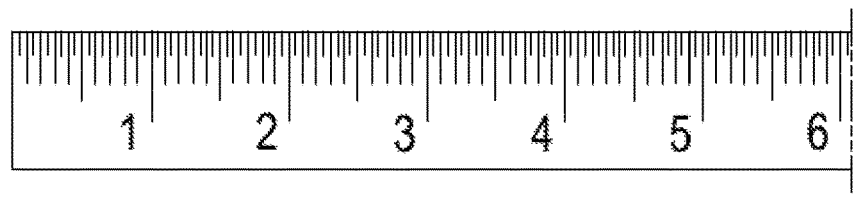

FIG. 1B shows the size of the resistive microfluidic pressure sensor 200 in relation to a coin.

First layer 202 and second layer 204

The first layer 202 and the second layer 204 may be of any suitable material. In particular, the first layer 202 and the second layer 204 may be of suitable material such that the resistive microfluidic pressure sensor 200 is able to display a high degree of flexibility and conformability, as well as being capable of withstanding a wide range of mechanical deformations such as pressing, stretching, shearing and bending. The first layer 202 is also the surface of the resistive microfluidic pressure sensor 200 which would be in contact with the force to be detected and measured. Thus, it is crucial for the material from which the first layer 202 is formed to be highly sensitive.

The first layer 202 and the second layer 204 may each be of the same material or of different material. For example, the first layer 202 and the second layer 204 may be formed from flexible elastic material. In particular, the flexible elastic material may be an elastomeric material. Elastomeric materials exhibit elastic properties because the polymer chains of the elastomer readily undergo torsional motion to permit uncoiling of the backbone chains in response to a force, with the backbone chains recoiling to assume the prior shape in the absence of the force. In general, elastomers deform when a force is applied, but then return to their original shape when the force is removed. The elasticity exhibited by elastomeric materials may be characterized by a Young's modulus. Elastomeric materials having a Young's modulus of about 1 Pa-1 TPa may be suitable for the present application. In particular, the Young's modulus of the elastomeric material may be about 10 Pa-100 GPa, 20 Pa-50 GPa, 50 Pa-1 GPa, 100 Pa-50 MPa, 500 Pa-10 MPa, or 750 Pa-1 MPa may be suitable for the present application. It would be clear to a skilled person that elastomeric materials having a Young's modulus outside of these ranges could also be utilized depending upon the needs of a particular application. Even more in particular, the first layer 202 and the second layer 204 may be formed from a material comprising silicone rubber, latex rubber, nitrile rubber, polyurethane (PU), polyvinylidene fluoride (PVDF), ethylene vinyl acetate (EVA), polyvinyl alcohol (PVA), polyethylene (PE), polypropylene (PP), polystyrene (PS), polydimethylsiloxane (PDMS), polybutyrate, polyethylene terephthalate (PET), polycarbonate (PC), polyimide (PI), or a combination thereof.

According to a particular aspect, the first layer 202 may be formed from silicone rubber and the second layer 204 may be formed from PDMS. It would be clear to a skilled person that other combinations of materials may also be possible. For example, the first layer-second layer combinations may be PDMS-PDMS, silicone rubber-silicone rubber, or PDMS-silicone rubber.

According to another particular aspect, each of the first layer 202 and the second layer 204 may be formed of multiple layers. For example, the multiple layers may be bonded together by suitable methods. For example, multilayer soft lithography may be used to form the first layer 202 and/or the second layer 204. The layers of elastomer may be cured separately and then bonded together. This scheme requires that cured layers possess sufficient reactivity to bond together. Either the layers may be of the same type, and are capable of bonding to themselves, or they may be of two different types, and are capable of bonding to each other. Other possibilities include the use an adhesive between layers and the use of thermoset elastomers.

The first layer 202 and the second layer 204 may be arranged to seal the carbon-based conductive liquid within the microfluidic channel 206 such that the carbon-based conductive liquid is interposed between the first layer 202 and the second layer 204. In particular, the first layer 202 and the second layer 204 may be bonded together to seal the microfluidic channel 206.

Microfluidic channel 206

The microfluidic channel 206 may be any suitable type of microfluidic channel. In particular, the microfluidic channel 206 must be suitable to be able to withstand the mechanical pressure applied on the surface of the resistive microfluidic pressure sensor 200.

The microfluidic channel 206 may be of any suitable shape. The microfluidic channel 206 may be a 2-dimensional or 3-dimensional structure. For example, the microfluidic channel 206 may be a straight channel, a 'S'-shaped channel or any other suitable shaped channel. The microfluidic channel 206 may have any suitable cross-sectional shape, such as square, rectangular, circular, semi-circular, ovular, and the like.

The microfluidic channel 206 may have suitable dimensions. In particular, the dimensions of the microfluidic channel 206 are selected to ensure that the volume of the microfluidic channel 206 is kept to a minimum so that less conductive fluid is required. Further, the dimensions are also such that the area on which force is applied and the sensitivity response of the resistive microfluidic pressure sensor 200 is high to ensure easier detection of changes in pressure. Since the microfluidic channel 206 is comprised in the first layer 202, the weight and elastic modulus of the first layer 202 are also taken into consideration. In particular, if the width of the microfluidic channel 206 is too wide, the first layer 202 may collapse under its own weight.

According to a particular aspect, the microfluidic channel 206 may have a width and/or length of 1 μm-100 mm. In particular, the width and/or length of the microfluidic channel 206 may be 10 μm-50 mm, 50 μm-10 mm, 100 μm-5 mm, 50 μm-1 mm, 100 μm-1000 μm, 250 μm-750 μm, 300 μm-600 μm, 450 μm-500 μm.

According to a particular aspect, the microfluidic channel 206 may be a straight channel. The straight channel may have any suitable dimensions. For example, the straight channel has a length l, width w and height h of 15 mm, 500 μm, and 80 μm.

Carbon-based conductive liquid

The microfluidic channel 206 comprises a suitable conductive liquid. The conductive liquid is enclosed within the microfluidic channel 206. Since the microfluidic channel 206 comprises a conductive liquid in liquid state, the resistive microfluidic pressure sensor 200 may be able to undergo an extreme degree of deformation without the conventional solid-state materials-associated plastic deformation, fracture and delamination.

The conductive liquid may be any suitable conductive liquid. For the purposes of the present invention, the conductive liquid may comprise fluids and hydrogels. The conductive liquid may have a low viscosity and high physiochemical stability. Since the resistive microfluidic pressure sensor 200 is sensing pressure by measuring resistance, it is also required for the conductive liquid to be high resistivity.

In particular, the conductive liquid may display low base electrical resistance and high stability of electrical resistance over time.

Suitable conductive liquids include, but are not limited to, metallic nanoparticles, ionic solutions, conductive grease and the like. The conductive liquid may be an organic-based conductive liquid. In particular, the conductive liquid may be a carbon-based conductive liquid. For example, the conductive liquid may be graphene, graphene oxide, reduced graphene oxide, graphite, fullerene, carbon nanotubes, carbon black, functionalised carbon-based nanomaterials, or a combination thereof. Even more in particular, the conductive liquid comprises graphene oxide.

Graphene oxide has good electrical properties and superior mechanical strength and flexibility. Further, graphene oxide is hydrophilic and water soluble, making it easier for the graphene oxide to be dispersed in solutions in a uniform manner. Graphene oxide also has a low surface tension of 6.16-16.83 mN/m depending on the media it interfaces with. This is advantageous as a very large surface tension, such as that of metallic liquids like eutectic GaIn metallic alloy, will prevent the liquid from occupying and forming the specific shape of the microfluidic channel 206, resulting in inaccurate sensing and measurement. Graphene oxide is also highly resistive with low differential conductivity ranges from $1$-$5\times10^{-3}$ S/cm, as well as non-corrosive, therefore making it suitable for use as a conductive liquid in the resistive microfluidic pressure sensor 200.

Any suitable concentration of graphene oxide may be used when used as the carbon-based conductive liquid. For example, the concentration of the graphene oxide may be $\geq 0.2$ mg/mL. In particular, the concentration of the graphene oxide may be $\geq 0.5$ mg/mL, $\geq 1.0$ mg/mL, $\geq 1.5$ mg/mL, $\geq 2.0$ mg/mL, $\geq 2.5$ mg/mL, $\geq 3.0$ mg/mL, $\geq 3.5$ mg/mL. Even more in particular, the concentration of the graphene oxide may be $\geq 3.0$ mg/mL.

According to a particular aspect, the carbon-based conductive liquid comprises highly concentrated graphene oxide nanosuspension comprising randomly oriented graphene oxide nanosheets dispersed homogeneously in distilled water.

The advantage of the conductive liquid being an organic-based conductive liquid, particularly a carbon-based conductive liquid is that the conductive liquid may be tuned in terms of electrical properties such as, but not limited to, conductivity and chemical reactivity, as well as in terms of material properties such as, but not limited to, structure, flexibility, thermal stability and hydrophobicity. Carbon-based conductive liquids are functionalizable and tunable for enhanced device sensitivity, specificity, and response time. Carbon-based conductive liquids are also biocompatible and non-corrosive, making it safe for handling and ensure durability of the pressure sensors to which the conductive liquid is added.

Method of fabricating the resistive microfluidic pressure sensor 200

Figure 2:
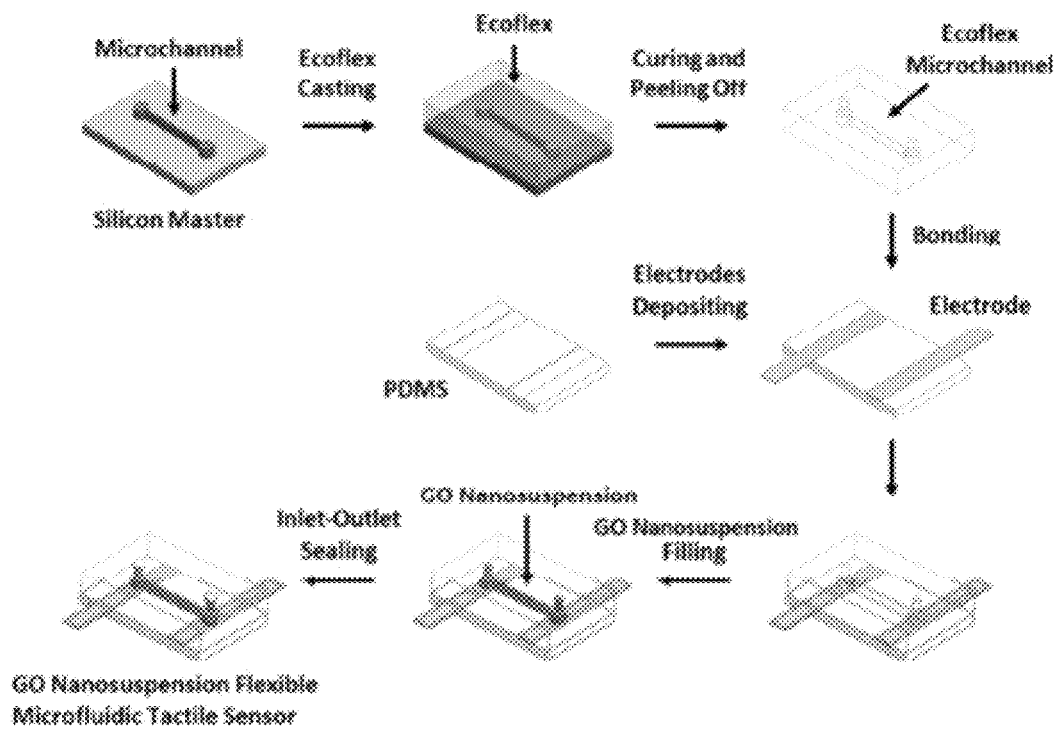
FIG. 2 shows a schematic representation of the fabrication of the resistive microfluidic pressure sensor of FIG. 1A.

A method of fabricating the resistive microfluidic pressure sensor 200 will now be described. The general method of fabricating the resistive microfluidic pressure sensor 200 is shown in FIG. 2.

The microfluidic channel 206 may be formed on the first layer using any suitable method. For example, the microfluidic channel 206 may be formed as an open channel in the first layer by cutting, stamping, casting, and the like. In particular, the first layer 202 comprising the microfluidic channel 206 may be formed from a master mold on a wafer using standard photolithography technique. For example, the wafer may be a silicon wafer and the master mold may be formed from a SU-8 photoresist. The first layer 202 may be formed from silicone rubber. Therefore, a soft silicone rubber may be mixed in a 1:1 (weight/weight) ratio of base to hardener. Any suitable base and hardener may be used for the purposes of the present invention. According to a particular aspect, the base may be any suitable elastomer. For example, the base may be, but not limited to, polyurethanes, silicone elastomers, urethane elastomers or polydimethylsiloxanes. In particular, the base may be Ecoflex™, DragonSkin™, Sylgard 184™. Even more in particular, the base may be platinum cured silicon rubber base and the hardener may be platinum cured silicon rubber hardener.

The mixture may then be poured onto the silicon wafer and cured at a suitable temperature for a first pre-determined period of time to form the first layer 202. In particular, the curing may be at a temperature of about 15-150° C. For example, the curing is at a temperature of 25-100° C., 50-75° C., 55-65° C. Even more in particular, the curing may be carried out at about 70° C. The first pre-determined period of time may be 10 minutes-24 hours. For example, the first pre-determined period of time may be 30 minutes-15 hours, 1-12 hours, 2-10 hours, 3-9 hours, 4-8 hours, 5-7 hours. In particular, the pre-determined period of time may be about 1 hour. The cured silicon rubber may then be removed from the mold.

Subsequently, an inlet 208 and an outlet 210 may be formed on the first layer 202. The inlet 208 and the outlet 210 may be formed by any suitable method. In particular, the inlet 208 and the outlet 210 may be formed by hole-punching.

The second layer 204 may be formed by any suitable method. In particular, the second layer 204 is formed of PDMS and is formed from mixing a prepolymer mix with a curing agent in a ratio of 10:1 (weight/weight). The mixture may be poured into a petri dish interposed with two electrodes, such as copper tapes, and cured at a suitable temperature for a second pre-determined period of time. In particular, the curing may be at a temperature of about 60-150° C. For example, the curing may be at a temperature of about 50-125° C., 75-100° C., 85-90° C. Even more in particular, the curing may be carried out at about 70° C. The second pre-determined period of time may be 30 minutes-48 hours. For example, the second pre-determined period of time may be 1-40 hours, 5-35 hours, 10-30 hours, 12-25 hours, 15-24 hours, 16-20 hours. In particular, the second pre-determined period of time may be about 2 hours.

Upon separate formation of the first layer 202 and the second layer 204, the first layer 202 and the second layer 204 are arranged to seal the microfluidic channel 206. In particular, the first layer 202 and the second layer 204 are bonded together. The bonding of the first layer 202 and the second layer 204 may be by any suitable method. For example, the bonding may be by, but not limited to, thermal treatment, ultraviolet ozone treatment, plasma cleaning treatment, high pressure bonding, chemical bonding, epoxy bonding, mechanical bonding, or a combination thereof. Even more in particular, the first layer 202 and the second layer 204 are bonded by a first thermal bonding, followed by ultraviolet ozone (UVO) treatment and oxygen plasma treatment. The thermal bonding may be carried out at about 70° C. for about 12 hours in a convection oven. The UVO treatment may be carried out for about 3 minutes and the oxygen plasma treatment may be carried out for about 2 minutes.

Once the first layer 202 and the second layer 204 are bonded together, the carbon-based conductive fluid is added into the microfluidic channel 206. However, it may also be possible to add the conductive fluid into the microfluidic channel 206 before the first layer 202 and the second layer 204 are bonded together. In particular, a pre-determined amount of graphene oxide having a concentration of about 5 mg/mL is injected into the microfluidic channel 206 through the inlet 208 using a needle syringe. The pre-determined amount of graphene oxide may be about 1 mL. The inlet 208 and the outlet 210 may then be sealed to confine the carbon-based conductive liquid within the microfluidic channel 206. The sealing may be by any suitable method. For example, the sealing may be by applying a UV adhesive onto the top surface of the inlet 208 and the outlet 210.

Use of the resistive microfluidic pressure sensor

Figure 3:
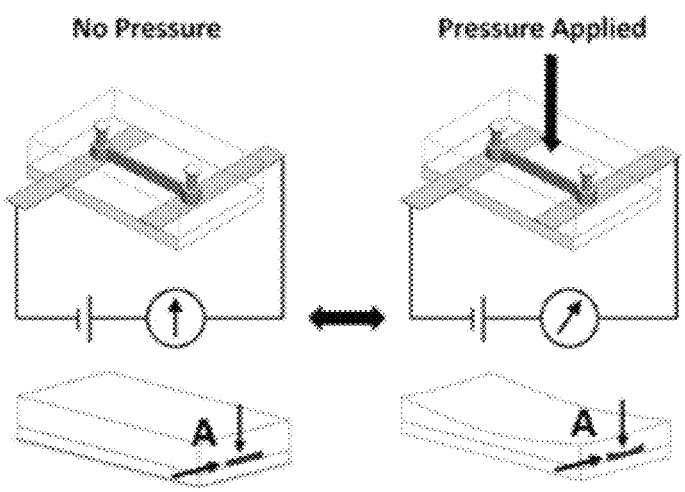
FIG. 3 shows a working mechanism of the resistive microfluidic pressure sensor.

The resistive microfluidic pressure sensor 200 operates based on deformability-dependent resistive sensing mechanism, as shown in FIG. 3, and as described by Equation (1):

$$R = \rho \frac{l}{A} \quad (1)$$

where R is the resistance of the carbon-based conductive liquid, ρ is the resistivity of the carbon-based conductive liquid, l is the length of the microfluidic channel 206, and A is the cross-sectional area of the microfluidic channel 206.

In particular, an application of a force on a surface of the resistive microfluidic pressure sensor 200 may cause deformation of the microfluidic channel 206 thereby decreasing the cross-sectional area of the microfluidic channel 206 and increasing the resistance of the carbon-based conductive liquid. The force may be a pressing force, a bending force, a shear force, and/or a stretching force.

Even more in particular, when an external mechanical pressure is applied on a surface of the resistive microfluidic pressure sensor 200, a minute compressive deformation of the microfluidic channel 206 occurs. This leads to a decrease in the cross-sectional area of the microfluidic channel 206 which, in turn, results in an increase in the resistance of the carbon-based conductive liquid across the microfluidic channel 206. On the other hand, upon release of the external pressure, due to the elastic property of the first layer 202, the microfluidic channel 206 will recover to its original state. This subsequently results in a decrease in the resistance of the carbon-based conductive liquid within the microfluidic channel 206. The specific increase and decrease in the electrical resistances of the carbon-based conductive liquid corresponds to the characteristic responses of different mechanical forces applied on the resistive microfluidic pressure sensor 200.

The resistive microfluidic pressure sensor 200 may be connected to at least one power source and/or an electrical property measuring device. For example, the power source may be a constant voltage source and the electrical property measuring device may be an ammeter, ohmmeter or voltmeter. According to a particular embodiment, an ohmmeter may be used as both the power source and the measuring device. A resistor or other circuit component may be placed in parallel or series with the electrodes, which would allow an ammeter to be used with a constant current source or a voltmeter to be used with a constant voltage source. A voltmeter may measure the voltage drop across a series resistor to determine the electrical properties of the electrodes.

The resistive microfluidic pressure sensor 200 being highly flexible, wearable and possessing excellent mechanical deformability and stability, as well as being simple and low-cost to manufacture makes it suitable for many applications such as in flexible wearable diagnostics and prognostic devices, as well as in real-time in situ health monitoring applications. The resistive microfluidic pressure sensor 200 is also capable of differentiating numerous types of user-applied forces such as pressing, stretching, shearing and bending forces, as well as characterizing and recognising different muscle-induced motions, such as hand muscle-induced motions.

Figure 11A:
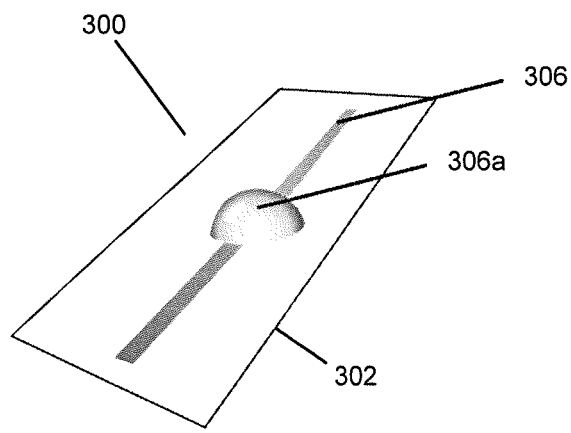
FIG. 11A shows a perspective view of an alternate embodiment of the resistive microfluidic pressure sensor of the present invention and FIGS. 11B to 11D show cross-sectional views of the pressure sensor of FIG. 11A in the original state, when in contact with a rough surface, and when in contact with a smoother surface, respectively.

The resistive microfluidic pressure sensor according to the present invention may also be capable of detecting various surface textures, such as those of varying roughness. For example, subtle changes in the surface texture may elicit different electrical signatures with the use of the sensor. An example of a resistive microfluidic pressure sensor capable of detecting surface roughness is shown in FIG. 11A. The resistive microfluidic pressure sensor 300 may comprise a first layer 302 which in turn may comprise a microfluidic channel 306 with a protrusion 306a. According to an alternative embodiment, the microfluidic channel 306 may comprise two or more protrusions, or an array of protrusions. The microfluidic channel 306 and the protrusion 306a may comprise a conductive liquid. The conductive liquid may be any suitable conductive liquid such as those described above. The second layer of the resistive microfluidic pressure sensor 300 comprising the electrodes is not shown. The fabrication of the resistive microfluidic pressure sensor 300 may be as described above with suitable modifications to enable the formation of the protrusion 306a in the microfluidic channel 306. Accordingly, the first layer 302 and the second layer may be made of materials as described above in relation to first layer 202 and second layer 204.

The protrusion may have dimensions suitable for the purposes of the present invention. For example, the protrusion 306a may have a height of about 1 μm-10 mm. In particular, the height of the protrusion 306a may be 10 μm-5 mm, 50 μm-3 mm, 75 μm-1 mm, 100 μm-800 μm, 200 μm-750 μm, 300 μm-600 μm, 450 μm-500 μm. Even more in particular, the height may be 1 mm-3 mm.

Figure 11B:
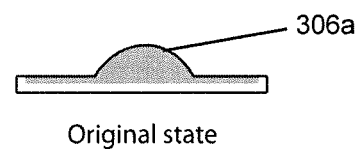
Figure 11C:
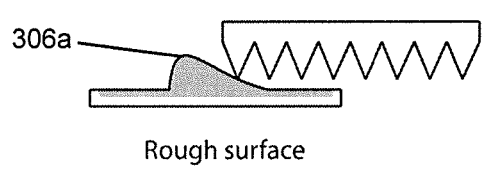
Figure 11D:
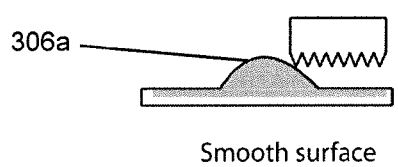

In general, the resistive microfluidic pressure sensor 300 may be fabricated to form a shear force-dependent resistive sensing mechanism as shown in FIGS. 11B to 11D. In particular, when an external mechanical shear force is applied on the protrusion 306a of the resistive microfluidic pressure sensor 300, the microfluidic channel 306 experiences a minute compressive deformation. This leads to a decrease in the cross-sectional area of the microfluidic channel 306, which, in turn, results in an increase in the resistance of the conductive liquid across the microfluidic channel 306. On the other hand, upon the release of the external pressure and due to the elastic property of the first layer 302, the microfluidic channel 306 will recover to its original state. This subsequently results in a decrease in the resistance of the conductive liquid. The specific increase and decrease in the electrical resistances of the conductive liquid correspond to the characteristic responses of different shear forces applied on the pressure sensor. FIG. 11B shows the original state of the protrusion 306a of the resistive microfluidic pressure sensor 300. FIG. 11C shows the deformation of the protrusion 306a upon contact with a rough surface and FIG. 11D shows the deformation of the protrusion 306a upon contact with a smoother surface. It can therefore be seen that when contacting a rougher surface, there is higher deformation of the protrusion 306a, thereby leading to a larger change in the electrical output.

According to a second aspect, there is provided a wearable device for pressure sensing. In particular, the wearable device comprises the resistive microfluidic pressure sensor as described above, and may be, but not limited to, a glove, watch, armband, headgear, socks, or an insole.

Whilst the foregoing description has described exemplary embodiments, it will be understood by those skilled in the technology concerned that many variations may be made without departing from the present invention.

Having now generally described the invention, the same will be more readily understood through reference to the following examples which are provided by way of illustration, and are not intended to be limiting.

EXAMPLE

Fabrication of resistive microfluidic pressure sensor

Highly concentrated graphene oxide (GO) nanosuspension of 5 mg/mL (Graphene Laboratories Inc., Calverton, N.Y.) was diluted to a low concentration of 20 μg/mL in DI water and then deposited on a 2% (v/v) 3-aminopropyltriethoxysilane (APTES, Sigma Aldrich, St. Louis, Mo.)-treated SiO2/Si substrate, followed by air drying. The surface topography of the as-deposited GO nanosheets was characterized using the tapping mode atomic force microscope (AFM) (Bruker, Billerica, Mass.). The lateral size distribution of the GO nanosheets was subsequently evaluated by analyzing the obtained AFM images using the ImageJ software (NIH, US). More than 500 GO nanosheets were examined and measured to obtain the lateral size distribution.

It was observed that the individual GO nanosheets had a thickness of approximately 1.2 nm, indicating that the GO nanosheets in the suspension were of monolayer. Further, the average size of the suspension of GO nanosheets was 0.487±0.286 μm (mean±standard deviation).

The dispersion of GO nanosheets was further characterized in the DI water by subjecting it to centrifugation at 2000×g for different durations of 5 seconds (s), 30 s, and 2 minutes. As a control, the GO nanosheets were also dispersed in a different solution, i.e., ethanol. The dispersion of GO nanosheets in DI water maintained its homogeneity even after undergoing intensive centrifugation. In contrast, those dispersed in ethanol formed sediments and settled to the bottom after centrifugation. All these highlight the homogeneity of the GO nanosheets dispersion in DI water and the suitability of this GO nanosuspension to be employed as the conductive liquid in the resistive microfluidic pressure sensor of the present invention. Once the GO nanosheets were formed, the resistive microfluidic pressure sensor was fabricated. In particular, the pressure sensor consisted of a first layer of a microfluidic channel in soft silicone rubber (Ecoflex™) and a second layer in PDMS. The soft silicone rubber had a density of 1070 kg/m$^3$ and Young's modulus of 250 kPa. The PDMS had a density of 970 kg/m$^3$ and Young's modulus of 2 MPa. The straight microfluidic channel possess a dimension of 15mm ×500 μm×80 μm (length×width× height).

The master mold for the first layer was fabricated from SU-8 photoresist on a silicon wafer using standard photolithography technique. In particular, soft silicone rubber was mixed in 1:1 (weight/weight) ratio base to hardener and poured onto the silanized wafer and cured at 70° C. for 1 hour to form the first layer. The cured silicone rubber was removed from the mold and fluidic inlet and outlet were formed through hole-punching (1.2 mm). The PDMS second layer was formed from a prepolymer mixed in 10:1 (weight/weight) ratio with curing agent using standard photolithography technique. The mixture was poured into a 60 mm petri dish interposed with two copper tapes and baked at 70° C. for 2 hours to form the second layer.

Various bonding treatments were performed on permutations of PDMS and silicone rubber layers: thermal bonding at 70° C. for 12 hours in a convection oven, UV ozone (UVO) treatment for 3 minutes, and oxygen plasma treatment for 2 minutes. The GO nanosuspension of 5 mg/mL was then filled in a 1 mL needle syringe and introduced into the microfluidic channel. UV adhesive was subsequently applied onto the top surface to seal the fluidic ports to confine the GO nanosuspension within the microfluidic device. In particular, the process for fabricating the pressure sensor is as shown in FIG. 2.

Bonding strength and mechanical deformation evaluation

In order to execute its designated functions robustly and effectively, the resistive microfluidic pressure sensor needs to display a high degree of flexibility and conformability as well as be capable of withstanding a wide range of mechanical deformations, for example, pressing, stretching, shearing and bending.

As such, the proper selection of materials to be used in the fabrication of our device is of paramount importance. To obtain the optimum combination of flexible materials for the pressure sensing application, three different material assemblies of PDMS-PDMS, Ecoflex-Ecoflex, and Ecoflex-PDMS were prepared. Three distinct bonding strategies were performed on the permutations of PDMS and silicone rubber substrates: thermal bonding at 70° C. for 12 hours, UV ozone (UVO) treatment for 3 minutes, and oxygen plasma treatment for 2 minutes.

The assemblies were subjected to flow leakage test to assess the bonding integrity of the first layer and the second layer of different materials. Food dye in red was filled in a 1 mL syringe and introduced into the microfluidic channel via flexible Tygon® tubing connections using a syringe pump. Flow rate was initiated at 100 μL/min and increased progressively until leakage was observed. Six different flow rates were chosen: 100, 200, 300, 500, 1000, and 1500 μL/min. Maximum flow rate was fixed at 1500 μL/min. To further validate its bonding integrity, peeling tests were performed using a universal loading device (5848 MicroTester, Instron, Norwood, Mass.) on the substrate assemblies described above. Briefly, the longitudinal ends of bonded assemblies measuring 40 mm by 20 mm were clamped on the grips of the Instron machine and loaded to failure with an extension rate of 10 mm/min. Next, the UVO-bonded GO nanosuspension pressure sensor was subjected to various mechanical deformations, such as stretching, twisting, shearing and bending, in order to evaluate the device flexibility, durability, and integrity. The integrity and confinement of GO nanosuspension within the microfluidic channel was then observed under a 4× optical microscope after each applied deformation.

Based on the experimental design, it was observed that flow leakage occurred to the thermal-bonded Ecoflex-Ecoflex assembly at an initial flow rate of 100 μL/min while the thermal-bonded Ecoflex-PDMS assembly experienced flow leakage at 200 μL/min. Nevertheless, apart from these two material assemblies, the dye solution successfully passed through all the microfluidic channels of other flexible materials without leakage, even at a high flow rate of 1500 μL/min. Considering that the total internal volume of the microfluidic channel and the highest flow rate applied were approximately 0.6 µL or 0.6 mm³ (i.e., length=15 mm, width=0.5 mm, and height=0.08 mm) and 1500 µL/min, respectively, the bonded assembly managed to withstand an intense influx of dye solution whose injection volume per minute was about 2500 times the total internal volume of the microfluidic channel, without destroying the bond. This verifies the robust bonding formed in all material assemblies that underwent oxygen plasma and UVO treatments.

Additionally, the pressure loss ΔP due to pipe-flow resistance arising from the flow rate Q across the microfluidic channel of length L and hydrodynamic diameter D can be simply described using the Darcy-Weisbach equation, i.e., Equation 2, $$\Delta P = \frac{8\rho f L Q^2}{\pi^2 D^5} \qquad (2)$$

where ρ is the fluid density and f is the Fanning friction coefficient. Given the maximum volumetric flow rate of 1500 µL/min, the pressure sensor could sustain a working pressure of more than 114 kPa, exceeding the requirements of most of the microfluidics-based applications. Consequently, except for the thermally bonded Ecoflex-Ecoflex and Ecoflex-PDMS assemblies, the rest of the bonded flexible materials exhibited extremely high bonding strength.

Figure 4A:
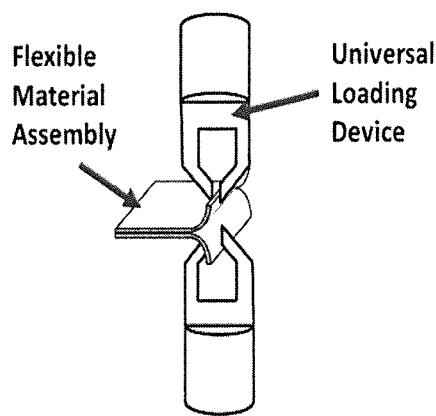
FIG. 4A shows a schematic illustration for a peel-test experimental set-up and FIG. 4B shows the ultimate peel strength (kPa) of the flexible material assemblies. The "*" represents statistically significant difference for $\rho < 0.05$ based on the t-test.

To further evaluate and quantify the bonding strength of the various flexible material assemblies, a peel test was performed using a universal loading device. FIG. 4A illustrates the schematic of the experimental set-up used in the peel test. By pulling the two layers of the pressure sensor completely apart, the bonding strength of the material assemblies were measured.

Figure 4B:
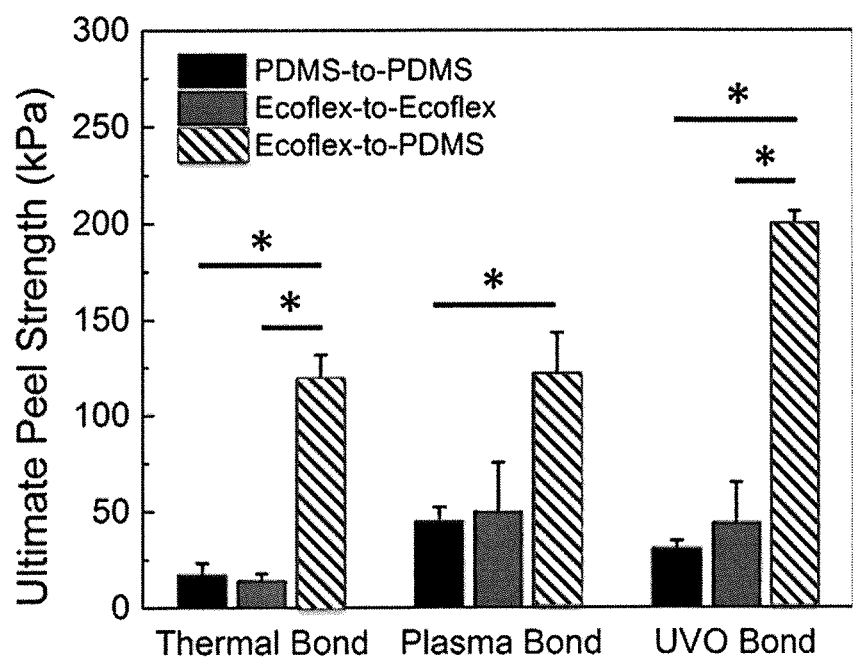

The results are shown in FIG. 4B. It was observed that among the nine flexible material permutations, the Ecoflex-PDMS assembly constantly displayed significantly higher peel strength (for $p<0.05$) than its PDMS-PDMS and Ecoflex-Ecoflex counterparts regardless of the bonding strategies used. In contrast, comparable peel strengths were noted between the PDMS-PDMS and Ecoflex-Ecoflex combinations, which were considerably lower than that of the Ecoflex-PDMS assembly. Examining the individual bonding techniques, it was observed that thermal bonding formed material assemblies with the lowest peel strengths while materials with the highest peel strengths could be prepared with UVO treatment.

Next, evaluating the peel strength of individual flexible material permutations, it was noted that the thermally bonded Ecoflex-Ecoflex exhibited the lowest peel strength of about 13.91±3.83 kPa while the UVO-treated Ecoflex-PDMS assembly displayed the highest ultimate peel strength of approximately 200±6.28 kPa. Therefore, based on all the experimental results derived from the flow leakage and peel tests, it was selected to fabricate a pressure sensor having the UVO-bonded Ecoflex-PDMS assembly which did not display any flow leakage at 1500 µL/min and exhibited the highest peel strength of around 200±6.28 kPa.

Figures 5, 6A, 6B:
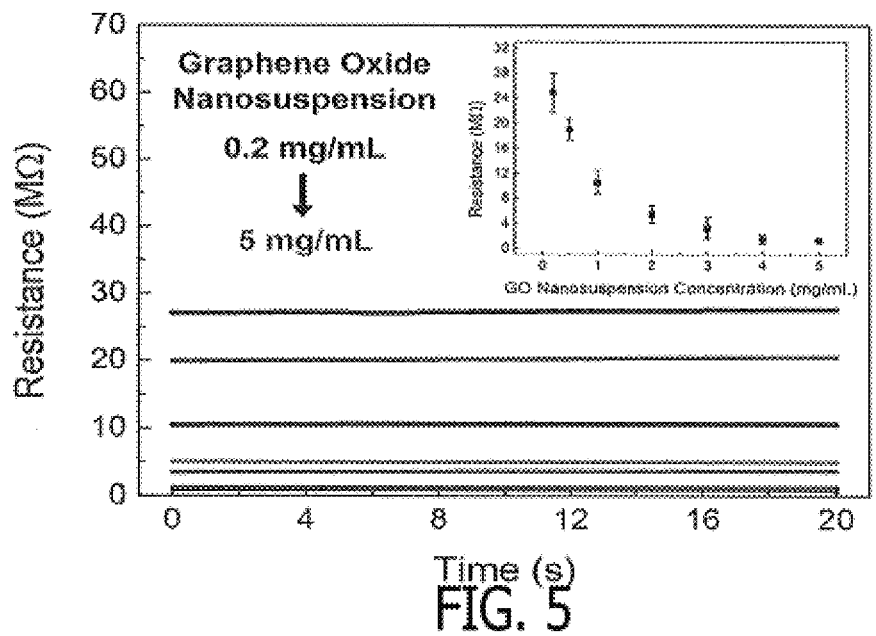
FIG. 5 shows the electrical resistance (M$\Omega$) stability of the GO suspension with different concentrations as a function of time. Inset shows the electrical resistance (MΩ) profile of the GO suspension as a function of its concentrations (mg/mL)
FIGS. 6A to 6D show the mechanical deformation characterization of the fabricated resistive microfluidic pressure sensor.

For a resistive pressure sensor to perform optimally, electrical baseline signal and cyclical stability are of utmost importance. Ideally, the conductive liquid of the pressure sensor shall display low base electrical resistance coupled with high stability of electrical resistance over time. Thus, it was sought to evaluate the stability of the electrical output of the fabricated pressure sensor over time as a function of the concentrations of GO nanosuspension. GO in nanosuspension was prepared in seven different concentrations, ranging from 0.2 to 5 mg/mL. The liquid suspension was then filled into the pressure sensor and the output signal of the pressure sensor was monitored over time. Interestingly, for all concentrations of GO nanosuspension, stable electrical output responses were observed. Nevertheless, the baseline resistance values of the tactile sensor decreased exponentially and reached saturation with minimal variations when the concentration of the GO suspension was increased to approximately 3 mg/mL, as seen in FIG. 5 and inset of FIG. 5. Consequently, GO nanosuspension with concentration above 3 mg/mL was derived to be a good candidate as the conductive liquid for the fabricated pressure sensor.

Figure 6C:
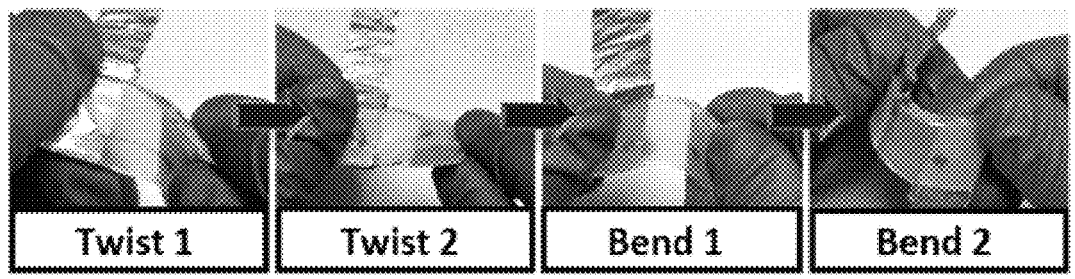
Figure 6D:
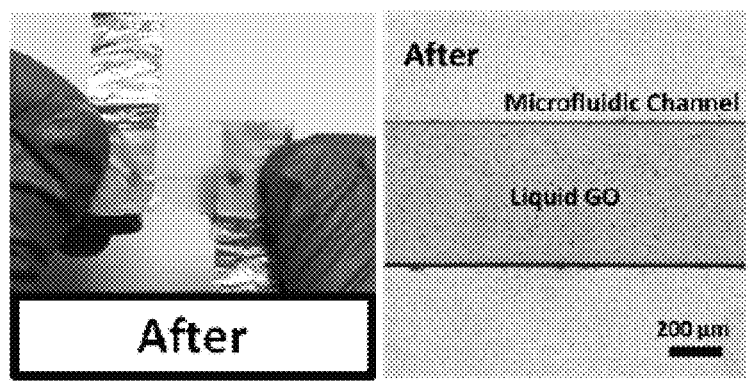

Following a series of characterizations on the individual components of the pressure sensor, i.e., the silicone rubber-PDMS microfluidic device and the GO nanosuspension, mechanical deformation characterization on the as-fabricated pressure sensor was performed to evaluate the integrity and confinement of the GO suspension within the microfluidic channel. FIG. 6A depicts the state of the GO nanosuspension being confined within the microfluidic channel before the pressure sensor was subjected to any user-applied deformation. First, the pressure sensor was stretched in a direction parallel to the microfluidic channel and it was observed that the GO suspension was well confined within the microfluidic channel as shown in FIG. 6B. Next, the same pressure sensor was put to various mechanical deformations like twisting and bending as shown in FIG. 6C. From these tests, the mechanical stability of the pressure sensor was noted as it experienced different forms of deformations and importantly, the well-maintained structure of the GO suspension within the microfluidic channel (FIG. 6D). In other words, as a liquid-state device, the fabricated pressure sensor displayed excellent mechanical deformability with superior working fluid confinement. Based on the advantage of the intrinsic mechanical feature of the liquid phase, these results demonstrated the distinctive characteristics and potential of the liquid-state device technology.

Pressure sensing and durability performance

In general, the pressure sensor is based on a deformability-dependent resistive sensing mechanism as shown in FIG. 3 which can be described by Equation 3, assuming small load-induced deformation based on the Hooke's Law in the linear elastic region. In the presence of applied force F of diameter d over the microfluidic channel of length l, the normalized change of resistance ($R/R_0$) equals to $$\frac{R}{R_0} = \frac{d}{l} \cdot \frac{EA}{EA-F} + \frac{l-d}{l} \cdot \frac{EA}{F} \ln \frac{EA}{EA-F} \qquad (3)$$

where E is the Young's modulus of the first substrate and A is the load contact area on the microfluidic channel. When an external mechanical force is applied on the surface of the pressure sensor, the microfluidic channel experiences a minute compressive deformation. This leads to a decrease in the cross-sectional area of the microfluidic channel, which, in turn, results in an increase in the resistance of the GO nanosuspension across the microfluidic channel. On the other hand, upon the release of the external pressure and due to the elastic property of the silicone rubber of the first layer, the microfluidic channel will recover to its original state. This subsequently results in a decrease in the resistance of the GO nanosuspension. The specific increase and decrease in the electrical resistances of the GO nanosuspension correspond to the characteristic responses of different mechanical forces applied on the pressure sensor.

Figure 7A:
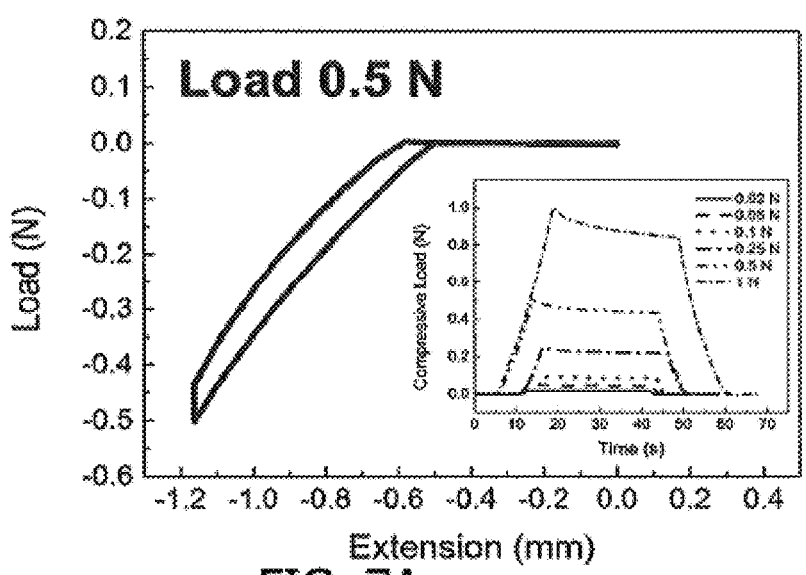
FIG. 7A shows the representative load (N) vs extension (mm) profile of a 0.5 N load applied on the resistive microfluidic pressure sensor. Inset shows the corresponding load (N) vs time (s) profile of different loads applied on the pressure sensor, ranging from 1 to 0.02 N.
Figure 7B:
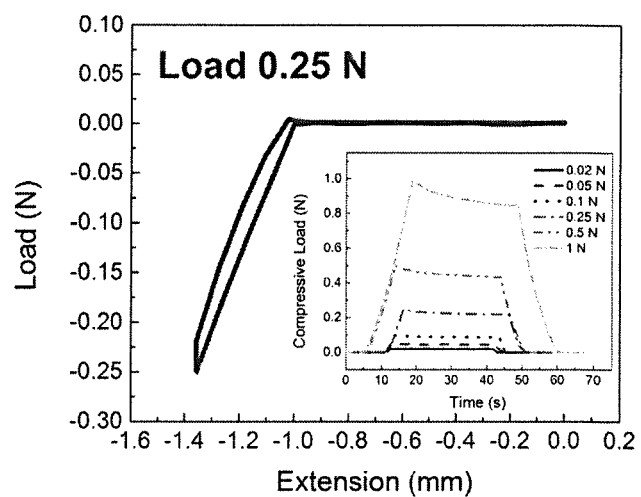
FIG. 7B shows the same as FIG. 7A except for a 0.25 N load applied on the resistive microfluidic pressure sensor.
Figure 7C:
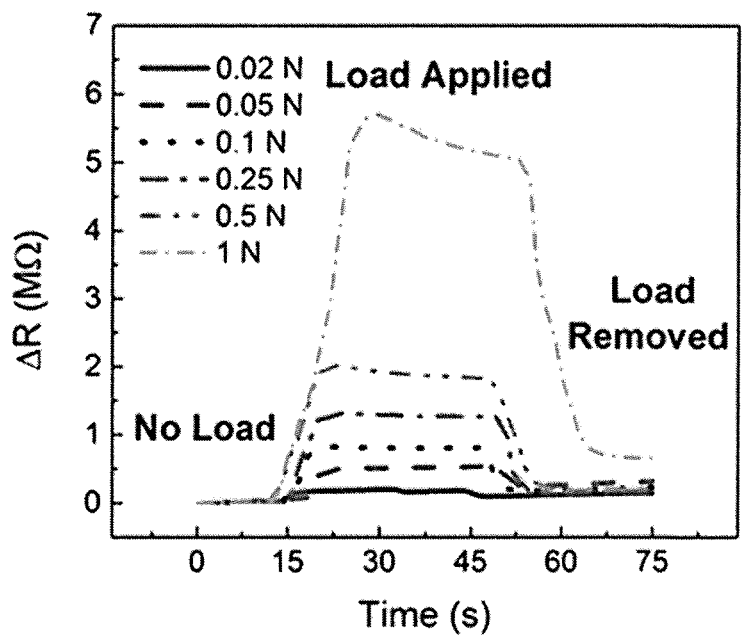
FIG. 7C shows the relative change in resistance (MΩ) vs time (s) profile of the pressure sensor upon application of different loads spanning from 1 to 0.02 N.

To characterize the pressure sensing performance and durability of the pressure sensor fabricated above against both the static and dynamic mechanical forces, the pressure sensor was subjected to different loading conditions. First, compressive ramp-hold-release load cycles were performed on the pressure sensor, starting from 1 N down to 0.02 N, using a universal load machine (5848 MicroTester, Instron, Norwood, Mass.) over a contact diameter of 5 mm. Specifically, six external loads were chosen: 1, 0.5, 0.25, 0.1, 0.05, and 0.02 N. FIGS. 7A and 7B illustrate the representative load vs extension profile of a 0.5 and 0.25 N load applied on the pressure sensor. The ramp rate was set up at 5 mm/min and the pressure sensor was held under compression for 30 seconds before releasing it to its initial position (Inset of FIGS. 7A and 7B). Subsequently, mechanical screws of three different masses of 1.8, 1.0 and 0.7 g were loaded and unloaded repeatedly on the pressure sensor to probe its electrical response. From the obtained results, it was noted that the pressure sensor showed consistent and steady responses to all applied loads down to 0.02 N (see FIG. 7C). At the same time, the relative change in the electrical resistance of the pressure sensor under each load condition was constant. This demonstrates the high stability of the pressure sensor.

Figure 7D:
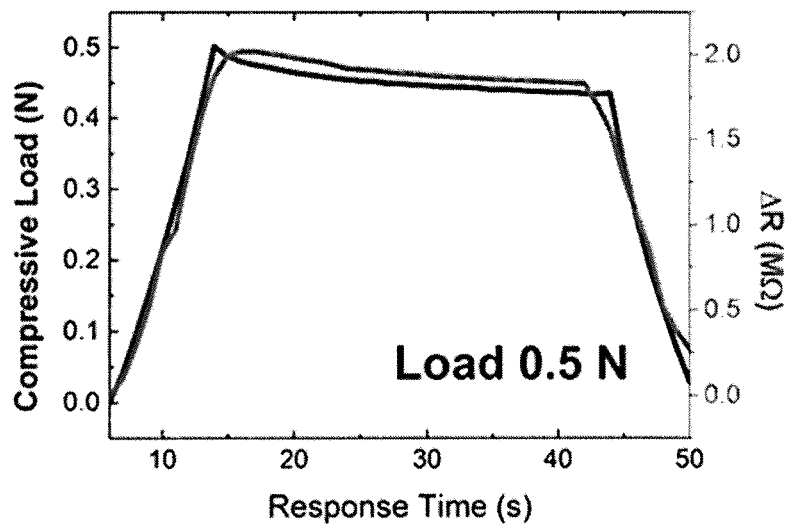
FIG. 7D shows superimposed profile of the compressive load (N) and relative change in resistance (MΩ) of the device as functions of response time under an applied load of 0.5 N.
Figure 7E:
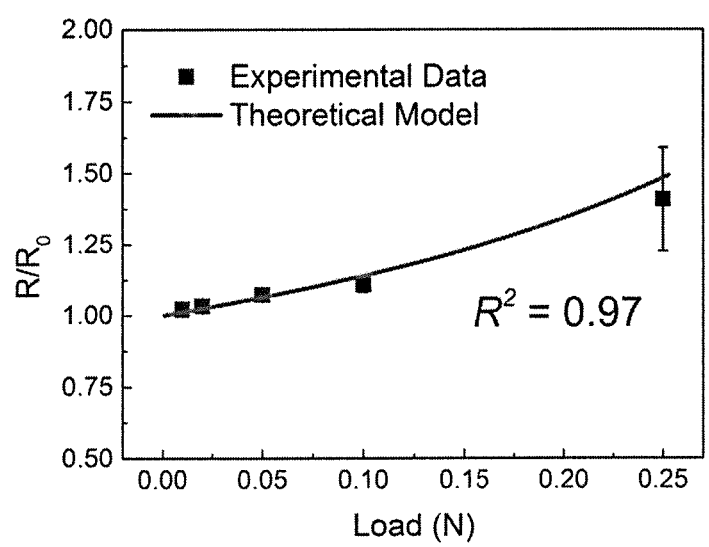
FIG. 7E shows relative rate of change in resistance ($R/R_0$) of the device as a function of load (N) for different loads of 0.02, 0.05, 0.1, and 0.25 N as obtained through experiments (black dots) and theoretical modeling (red line) with a high correlation coefficient ($R^2=0.97$)

Moreover, by superimposing and comparing the profiles of the compressive load and relative resistance change as functions of response time, the fast response displayed by the pressure sensor was noted (FIG. 7D). Remarkably, it is important to highlight that the experimentally obtained electrical responses of the pressure sensor against the applied compressive loads matched those derived based on the theoretical model closely, with a high correlation coefficient (i.e., $R^2=0.97$) (FIG. 7E). Based on this, it was concluded that the pressure sensor operated with a sensitivity of approximately $3.38\times10^{-2}$ $kPa^{-1}$.

Figure 7F:
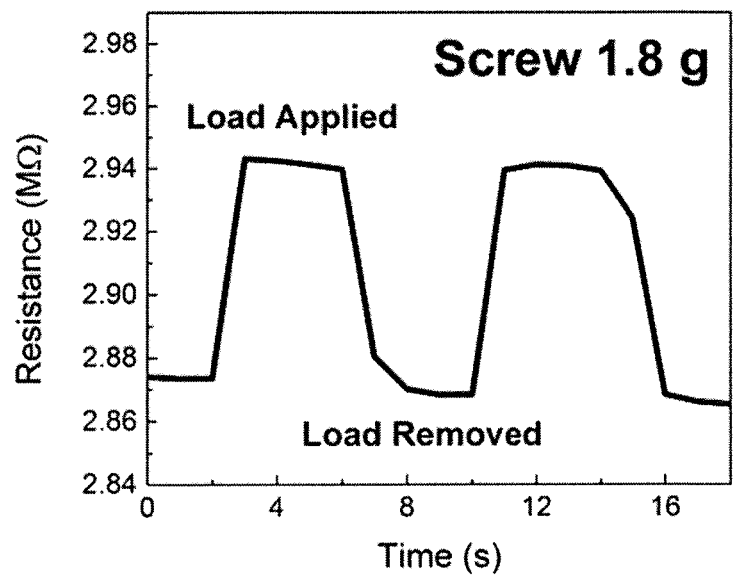
FIGS. 7F to 7H show the resistance (MΩ) vs time (s) profiles of the pressure sensor upon cyclical loading and unloading of mechanical screws of 1.8 g (FIG. 7F), 1.0 g (FIG. 7G) and 0.7 g (FIG. 7H). Inset of FIG. 7H shows the actual 0.7 g mechanical screw being loaded on the pressure sensor.
Figure 7G:
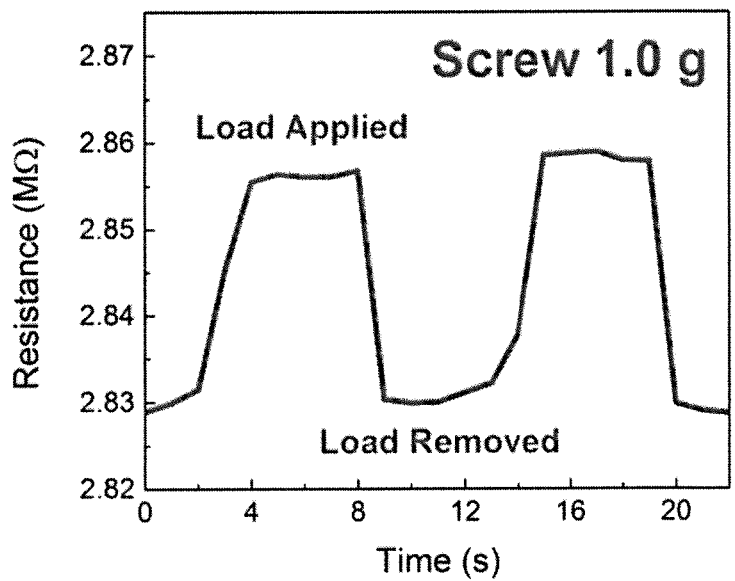
Figure 7H:
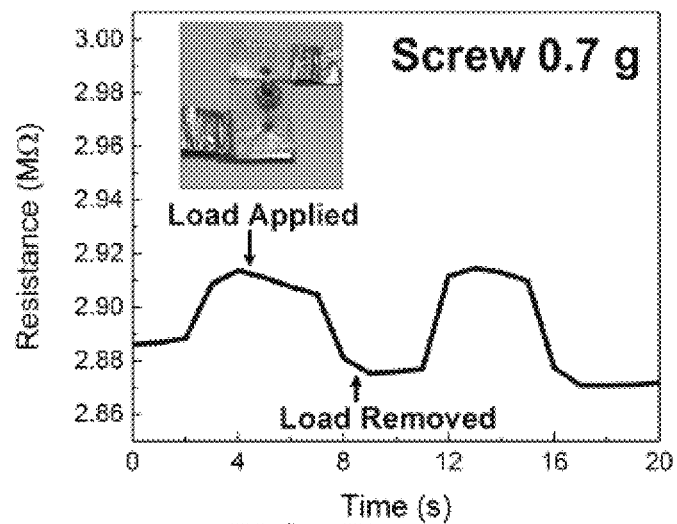

Further, for dynamic load measurement, numerous loading-unloading tests using mechanical screws with masses of 1.8 g, 1.0 g, and 0.7 g, corresponding to forces of approximately 0.018 N, 0.01 N, and 0.0007 N, respectively. The mechanical screws were applied and removed repeatedly to validate the pressure sensing capability and stability over a range of dynamic forces. Similarly, the pressure sensor revealed steady electrical responses to all three loads, and also the relative change in the device resistance was constant for every load condition (FIGS. 7F and 7H). It was also shown that the pressure sensor was able to detect cyclical loads down to 0.007 N steadily with distinguishable resolution (FIG. 7H).

Figure 8A:
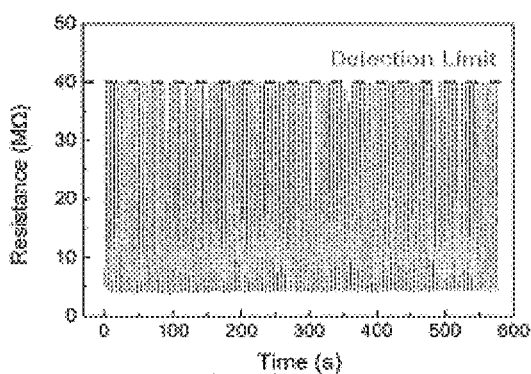
FIG. 8A shows the resistance profile of the pressure sensor subjected to 100 cycles of cyclical load switching and FIG. 8B shows the enlarged view of the part of the resistance profile of the pressure sensor in (g) after 95 loading-unloading cycles.
Figure 8B:
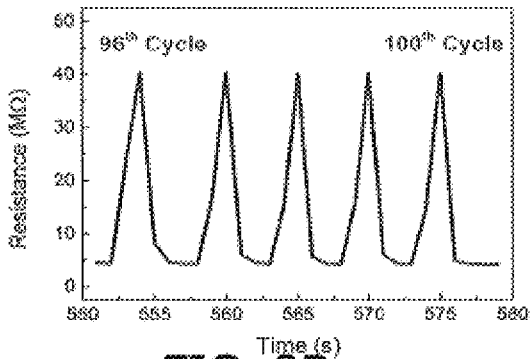

As such, it was observed that the working range of the pressure sensor fell in the range of about 0.007 N up to roughly 0.25 N. In addition to all the pressure sensing performance evaluations, the stability and durability of the pressure sensor was further probed through cyclical load switching characterization (FIG. 8A and FIG. 8B). The pressure sensor was subjected to 100 cycles of continuous loading-unloading test. Based on the experimental results, it was observed that there were negligible variations in its resistance profile over time. Importantly, the pressure sensor exhibited exceptional signal stability and high durability after undergoing intensive loading-unloading cycles.

Mechanical force differentiation

Figure 9A:
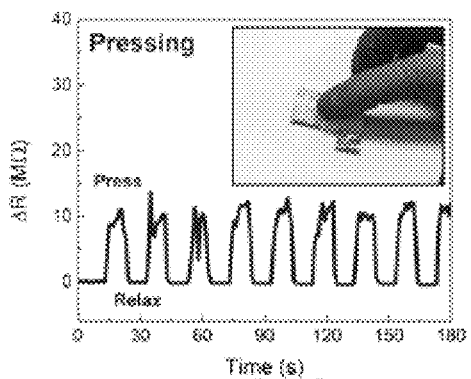
FIG. 9 shows the plots showing the relative changes in the electrical resistances of the pressure sensor when it was subjected to dynamic loading and unloading cycles: (A) pressing, (B) stretching, and (C) bending.
Figure 9B:
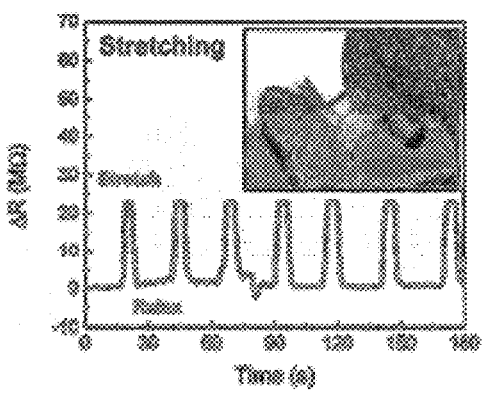
Figure 9C:
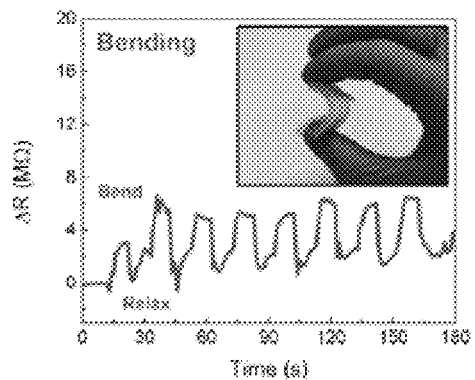

Apart from pressing forces, due to the high degree of flexibility of the fabricated pressure sensor, it could, in fact, be utilized to detect and differentiate other types of mechanical forces too, such as stretching and bending forces. The pressure sensor was subjected to cyclical pressing, stretching, and bending forces and its electrical responses were examined as shown in FIGS. 9A-9C. Remarkably, the electrical response curves generated by the pressure sensor were characteristic of the distinct types of mechanical forces the device was being subjected to. Moreover, the high signal-to-noise ratios in all three types of force measurements was noted, further showing the sensing and differentiating capability of the pressure sensor.

To demonstrate the applicability and wearability of the pressure sensor, the pressure sensor was attached to a human hand and its capability in recognizing different hand gestures was probed. As a proof-of-concept of its application in detecting and differentiating various hand muscle-induced motions, the pressure sensor was attached to finger and wrist and its dynamic pressure responses were monitored while different hand motions were executed (see FIGS. 10A-10D). Throughout all the experiments, the electrical resistance of the pressure sensor was recorded simultaneously using a digital multimeter with data logging function (such as EX542, Extech Instruments, Nashua, N.H.) while the device was subjected to the different types of external pressures.

The electrical output of the device placed on an index finger was investigated when it was subjected to both forward (FIG. 10A) and backward (FIG. 10B) flexing motions. For the forward flexing motion, the sensor was put on the finger ventral side, while the sensor was attached to the finger dorsal side for the backward flexing motion. The sensor output was characterized as a function of the difference in flexions of the finger muscles. For both flexing motions, higher peaks in the electrical output were observed when the index finger was flexed. The electrical resistance of the pressure sensor returned to its initial state when the finger was extended. Distinct signal patterns were noted from the two gestures of finger flexion and extension. Larger forces were exerted when the pressure sensor experienced forward flexing as compared to when it underwent backward flexing. Importantly, by repeating the same forward and backward flexing motions for numerous times, the device stability was exemplified.

Figure 10A:
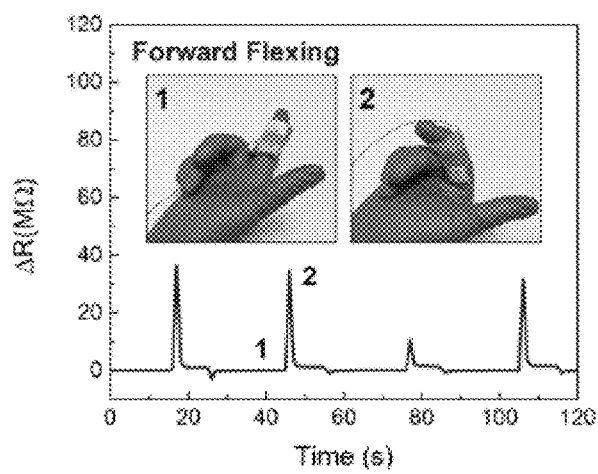
FIG. 10A shows forward flexing and FIG. 10B shows backward flexing.
Figure 10B:
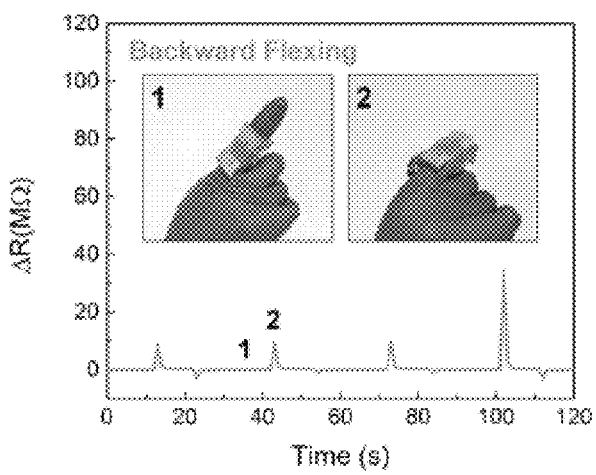
Figure 10C:
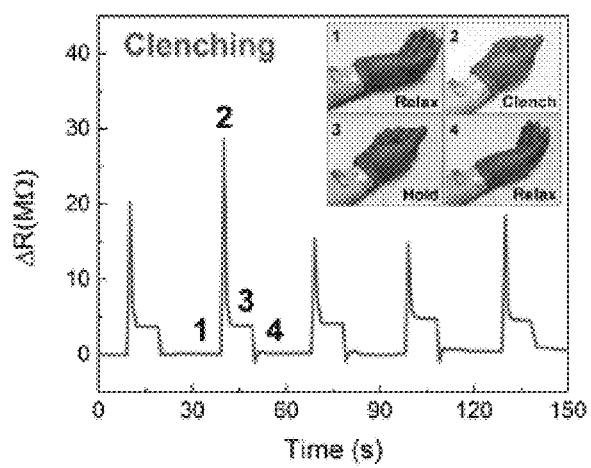
FIG. 10C shows the relative change in the resistance response of the pressure sensor against the dynamic fist clenching motion.
Figure 10D:
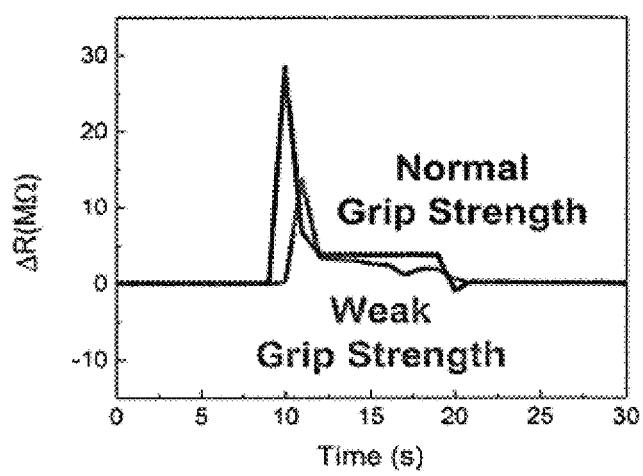
FIG. 10D shows the characteristic responses of normal handgrip and weak handgrip.

The force recognition and differentiation capability of the pressure sensor was investigated by attaching it to the wrist proximal to the pronator quadratus muscle and detecting the electrical output produced from the fist-clenching motion corresponding to handgrip strength. The fist-clenching gesture was divided into four steps: "relax", "clench", "hold", and "relax" (see Inset of FIG. 10C) and the respective electrical responses generated from these motions were recorded (FIG. 10C). For each step, a unique output was noted. Interestingly, the pressure sensor was capable of distinguishing the different signals in the "hold" motion (FIG. 10D). This particular step, in fact, is closely correlated to the handgrip strength. The relative changes in the electrical resistances of the pressure sensor under the conditions of normal grip and weak grip were clearly different and distinguishable. During normal condition, a pulse waveform with sharp peak coupled with a straight shoulder could be observed. More specifically, the typical waveform obtained for the "hold" motion would be in the shape of a horizontal straight line. Conversely, under a weak grip condition, the "hold" waveform would be an irregular line. These results demonstrated that the subtle differences in the handgrip strength as well as the dynamic response of the sustained muscle contraction could be identified with the fabricated pressure sensor. Significantly, this highlighted its application as a wearable diagnostic and prognostic device for health monitoring in real-time under different conditions, in general, and for grip strength and hand dexterity assessment, in particular. Hand dexterity requires coordination of various muscle groups and is an important requirement for daily living activities. Poor grip strength in the elderly is normally related to sarcopenia and has been associated with under-nutrition, chronic diseases, cognitive impairment, and even mortality. In patients, the assessment of grip strength has predictive potential for hospitalization length, postoperative complications and rehabilitation progression.

The invention claimed is:

1. A resistive microfluidic pressure sensor comprising:
a first layer comprising a microfluidic channel, the microfluidic channel comprising a conductive liquid; and
a second layer comprising at least two electrodes, the at least two electrodes being adapted to measure resistance of the conductive liquid upon deformation of the microfluidic channel as a result of a change in force applied on a surface of the sensor;
wherein the first layer and the second layer are arranged to seal the conductive liquid within the microfluidic channel, the conductive liquid being interposed between the first layer and the second layer.

2. The sensor according to claim 1, wherein the sensor is flexible.

3. The sensor according to claim 1, wherein the first layer and the second layer are of the same or different material, and are formed from an elastomeric material.

4. The sensor according to claim 1, wherein the first layer and the second layer are of the same or different material, wherein the material comprises silicone rubber, latex rubber, nitrile rubber, polyurethane (PU), polyvinylidene fluoride (PVDF), ethylene vinyl acetate (EVA), polyvinyl alcohol (PVA), polyethylene (PE), polypropylene (PP), polystyrene (PS), polydimethylsiloxane (PDMS), polybutyrate, polyethylene terephthalate (PET), polycarbonate (PC), polyimide (PI), or a combination thereof.

5. The sensor according to claim 4, wherein the first layer comprises silicone rubber and the second layer comprises PDMS.

6. The sensor according to claim 1, wherein the change in force is from a change in pressing force, bending force, shearing force or stretching force.

7. The sensor according to claim 1, wherein application of a force on the surface of the sensor causes deformation of the microfluidic channel thereby decreasing the cross-sectional area of the microfluidic channel and increasing the resistance of the conductive liquid.

8. The sensor according to claim 1, wherein the conductive liquid comprises nanoparticles.

9. The sensor according to claim 8, wherein the nanoparticles are metallic nanoparticles, carbon-based nanoparticles, or a combination thereof.

10. The sensor according to claim 1, wherein the conductive liquid is a carbon-based conductive liquid.

11. The sensor according to claim 10, wherein the carbon-based conductive liquid comprises: graphene, graphene oxide, reduced graphene oxide, graphite, fullerene, carbon nanotubes, carbon black, functionalized carbon-based nanomaterials, or a combination thereof.

12. The sensor according to claim 10, wherein the carbon-based conductive liquid is a graphene oxide having a concentration greater or equal to 3.0 mg/mL.

13. The sensor according to claim 1, wherein the second layer is formed of multiple layers.

14. The sensor according to claim 1, wherein the microfluidic channel comprises a protrusion, the protrusion being configured to detect changes in surface texture.

15. The sensor according to claim 14, such that application of a shear force on the protrusion leads to deformation of the microfluidic channel, thereby decreasing the cross-sectional area of the microfluidic channel and increasing the resistance of the conductive liquid.

* * * * *